United States Patent
Griffiths et al.

(10) Patent No.: US 12,144,574 B2
(45) Date of Patent: Nov. 19, 2024

(54) SYSTEM AND METHOD FOR ASSISTING TOOL EXCHANGE

(71) Applicant: INTUITIVE SURGICAL OPERATIONS, INC., Sunnyvale, CA (US)

(72) Inventors: Paul G. Griffiths, Santa Clara, CA (US); Xingchi He, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 431 days.

(21) Appl. No.: 17/289,999

(22) PCT Filed: Oct. 31, 2019

(86) PCT No.: PCT/US2019/059172
§ 371 (c)(1),
(2) Date: Apr. 29, 2021

(87) PCT Pub. No.: WO2020/092775
PCT Pub. Date: May 7, 2020

(65) Prior Publication Data
US 2022/0000571 A1 Jan. 6, 2022

Related U.S. Application Data

(60) Provisional application No. 62/753,762, filed on Oct. 31, 2018.

(51) Int. Cl.
*A61B 34/00* (2016.01)
*A61B 34/10* (2016.01)
(Continued)

(52) U.S. Cl.
CPC .............. *A61B 34/70* (2016.02); *A61B 34/10* (2016.02); *A61B 90/06* (2016.02);
(Continued)

(58) Field of Classification Search
CPC ......... A61B 34/70; A61B 34/10; A61B 90/06; A61B 2034/104; A61B 2090/064;
(Continued)

(56) References Cited

U.S. PATENT DOCUMENTS 4,852,928 A * 8/1989 Monforte ................. B25J 15/04
294/902
6,645,196 B1 11/2003 Nixon et al.
(Continued)

FOREIGN PATENT DOCUMENTS

EP 1815950 A1 * 8/2007 ............. A61B 34/30
WO WO-2017210497 A1 12/2017

OTHER PUBLICATIONS

International Search Report and Written Opinion for Application No. PCT/US2019/059172, mailed Feb. 13, 2020, 19 pages.
(Continued)

*Primary Examiner* — Alicia M. Choi
(74) *Attorney, Agent, or Firm* — Artegis Law Group, LLP (57) ABSTRACT

A system and method of assisting tool exchange includes a computer-assisted device having a manipulator configured to have at least one tool of multiple tools mounted thereon and a control unit coupled to the manipulator. The control unit is configured to detect initiation of a tool exchange, locate a source of a replacement tool to be mounted to the manipulator, determine, based on the located source, a configuration of the manipulator that facilitates mounting of the replacement tool to the manipulator, and command movement of the manipulator into the configuration. In some embodiments, the control unit is configured to determine the configuration further based on a type of the source of the replacement tool. In some embodiments, to locate the
(Continued)

source of the replacement tool, the control unit is configured to locate at least a part of an assistant or locate a tool holding device.

27 Claims, 5 Drawing Sheets

(51) Int. Cl.
    *A61B 90/00*     (2016.01)
    *B25J 15/04*     (2006.01)

(52) U.S. Cl.
    CPC ..... B25J 15/0466 (2013.01); *A61B 2034/104* (2016.02); *A61B 2090/064* (2016.02); *A61B 2090/066* (2016.02)

(58) Field of Classification Search
    CPC ........ A61B 2090/066; A61B 2034/302; A61B 34/20; A61B 90/50; A61B 90/90; A61B 34/30; B25J 15/0466
    See application file for complete search history.

(56) References Cited

U.S. PATENT DOCUMENTS

| | | | |
|---|---|---|---|
| 10,772,689 B2 | 9/2020 | Gomez et al. | |
| 11,457,983 B1* | 10/2022 | Roh | A61B 34/25 |
| 2001/0021337 A1* | 9/2001 | Murata | B25B 5/061 |
| | | | 29/563 |
| 2006/0060216 A1* | 3/2006 | Woo | A47L 9/0009 |
| | | | 15/1 |
| 2009/0192523 A1* | 7/2009 | Larkin | A61B 34/20 |
| | | | 606/130 |
| 2010/0174410 A1* | 7/2010 | Greer | A61B 34/37 |
| | | | 700/264 |
| 2011/0190790 A1* | 8/2011 | Summerer | A61B 34/76 |
| | | | 606/130 |
| 2012/0245596 A1 | 9/2012 | Meenink | |
| 2013/0103192 A1* | 4/2013 | Huettenhofer | B25J 9/162 |
| | | | 700/245 |
| 2015/0257841 A1 | 9/2015 | Dachs, II | |
| 2016/0035079 A1* | 2/2016 | Tenney | G06T 7/80 |
| | | | 382/153 |
| 2016/0151120 A1 | 6/2016 | Kostrzewski et al. | |
| 2016/0207202 A1* | 7/2016 | Lee | G05B 19/40938 |
| 2018/0049794 A1* | 2/2018 | Swayze | A61B 90/98 |
| 2020/0060774 A1 | 2/2020 | Nelson et al. | |
| 2020/0155244 A1 | 5/2020 | Sevimli et al. | |
| 2021/0015573 A1 | 1/2021 | Tsao et al. | |
| 2021/0128248 A1* | 5/2021 | Cohen | A61B 18/14 |
| 2021/0153924 A1* | 5/2021 | Swayze | A61B 90/98 |
| 2024/0122660 A1* | 4/2024 | Kostrzewski | B25J 19/06 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/059172, mailed on May 14, 2021, 15 pages.

* cited by examiner

SYSTEM AND METHOD FOR ASSISTING TOOL EXCHANGE

RELATED APPLICATIONS

This application is a U.S. National Stage patent application of International Patent Application No. PCT/US2019/059172, filed Oct. 31, 2019, the benefit of which is claimed, and claims priority to and benefit of U.S. Provisional Patent Application No. 62/753,762, filed Oct. 31, 2018 and entitled "System and Method for Assisting Tool Exchange," each of which is incorporated by reference herein in its entirety.

TECHNICAL FIELD

The present disclosure relates generally to control of devices with repositionable arms and more particularly to assisting with the exchange of tools mounted to the repositionable arms.

BACKGROUND

More and more devices are being replaced with autonomous and semiautonomous electronic devices. This is especially true in industrial, entertainment, educational, and other settings. As a medical example, the hospitals of today with large arrays of autonomous and semiautonomous electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical and other medical instruments are being replaced by computer-assisted medical devices.

These electronic devices provide both advantages and challenges to the personnel operating them. Many of these electronic devices may be capable of autonomous or semi-autonomous motion of one or more repositionable arms and/or tools. For example, in order to facilitate flexible use of the electronic devices, the electronic devices may be configured to have different tools mounted to a repositionable arm so that, at different times, the different tools may be used to perform different tasks in a workspace (e.g., an interior anatomy of a patient as a medical example). However, geometries of the electronic devices, the repositionable arms, the tools, and/or other objects in the workspace may make is difficult to exchange tools while safely and reliably operating the electronic devices.

Accordingly, improved methods and systems for assisting with the exchange of tools mounted to repositionable arms are desirable.

SUMMARY

Consistent with some embodiments, a computer-assisted device includes a manipulator configured to have at least one tool of multiple tools mounted thereon and a control unit coupled to the manipulator. The control unit is configured to detect initiation of a tool exchange, locate a source of a replacement tool to be mounted to the manipulator, determine, based on the located source, a configuration of the manipulator that facilitates mounting of the replacement tool to the manipulator, and command movement of the manipulator into the configuration.

Consistent with some embodiments, a method performed by a control unit includes detecting initiation of a tool exchange, locating source of a replacement tool to be mounted to the manipulator, determining, based on the located source, a configuration of a manipulator of a computer-assisted device that facilitates mounting of the replacement tool to the manipulator, the manipulator being configured to have at least one tool of multiple tools mounted thereon, and commanding movement of the manipulator into the configuration.

Consistent with some embodiments, a non-transitory machine-readable medium comprising a plurality of machine-readable instructions which when executed by one or more processors associated with a computer-assisted device are adapted to cause the one or more processors to perform any of the methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like-may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of the devices and elements in terms of their state in three-dimensional space. As used herein, the term "position" refers to the translational placement of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, and for a device with repositionable arms, the term "proximal" refers to toward the base of the device and "distal" refers to away from the base.

Aspects of the invention are described primarily in terms of an implementation using a computer-aided medical system such as a da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on any surgical systems such as the da Vinci® Surgical Systems are merely exemplary and are not to be considered as limiting the scope of the inventive aspects disclosed herein. For example, any reference to surgical instruments and surgical methods is non-limiting as the tools, systems, and methods described herein may be used for animals, human cadavers, animal cadavers, portions of human or animal anatomy, tissue removed from human or animal anatomies (with or without return to a human or animal anatomy), non-surgical diagnosis, industrial systems, and general robotic or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

Figure 1:
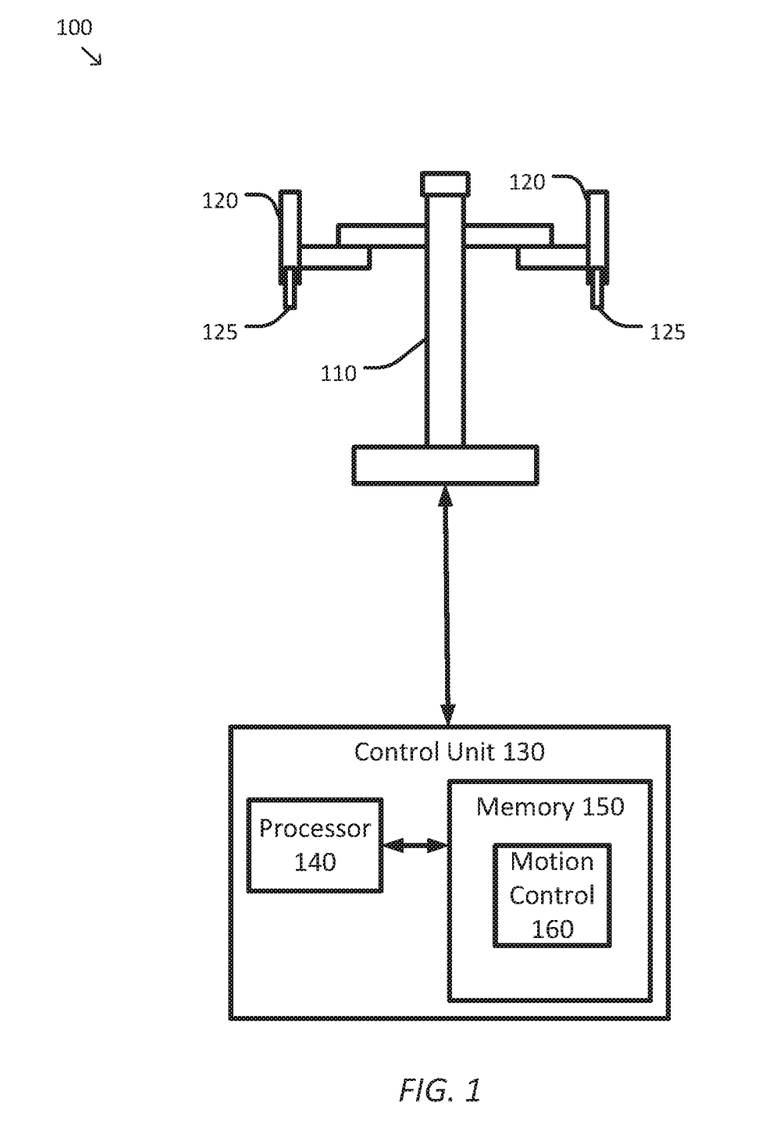
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a computer-assisted device 110 with one or more repositionable arms 120. Each of the one or more repositionable arms 120 may support one or more tools 125. In some examples, computer-assisted device 110 may be consistent with a computer-assisted medical device such as a computer-assisted non-invasive diagnosis device and/or a computer-assisted surgical device. The one or more tools 125 may include instruments, imaging devices, and/or the like. In some medical examples, the instruments may include medical instruments, such as clamps, grippers, retractors, cautery tools, suction tools, suturing devices, and/or the like. In some medical examples, the imaging devices may include endoscopes, cameras, ultrasonic devices, fluoroscopic devices, and/or the like.

Computer-assisted device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in control unit 130. Control unit 130 may be implemented as a stand-alone subsystem and/or as a board added to a computing device or as a virtual machine.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

In some embodiments, computer-assisted system 100 may be found in a medical setting such as an operating room and/or an interventional suite. And although computer-assisted system 100 includes only one computer-assisted device 110 with two repositionable arms 120, one of ordinary skill would understand that computer-assisted system 100 may include any number of computer-assisted devices with repositionable arms and/or tools of similar and/or different design from computer-assisted device 110. And although computer-assisted device 110 is shown as a stand-alone unit (e.g., with a base on the floor), computer-assisted device 110 may be wall-mounted, ceiling mounted, mounted to a table and/or workspace, and/or the like. In some examples, each of the computer-assisted devices may include fewer or more repositionable arms 120 and/or tools 125.

Motion control module 160 may support autonomous and/or semiautonomous control of computer-assisted device 110. Motion control module 160 may additionally include one or more application programming interfaces (APIs) for receiving position, motion, and/or other sensor information from computer-assisted device 110, exchanging position, motion, and/or collision avoidance information with other control units regarding other devices, and/or planning and/or assisting in the planning of motion for computer-assisted device 110, repositionable arms 120, tools 125, and/or the like. In addition, motion control module 160 may provide commands to one or more actuators used to control positions and/or orientations of repositionable arms 120, tools 125, and/or the like. And although motion control module 160 is depicted as a software module, motion control module 160 may be implemented using hardware, software, and/or a combination of hardware and software.

One of the tasks of motion control module 160 is to help support the swapping and/or exchange of the one or more tools 125 on the one or more repositionable arms 120 so that during a procedure a first tool 125 (e.g., an "old" or "previous" tool) may be dismounted from a repositionable arm 120 and a second tool 125 (e.g., a "new" or "replacement" tool) may then be mounted to the repositionable arm 120 (e.g., second tool 125 is exchanged as a new or replacement for first tool 125). In practice, this typically involves at least partially retracting and/or withdrawing first tool 125 from a workspace, dismounting first tool 125 from repositionable arm 120, mounting second tool 125 to the repositionable arm 120, and then reinserting second tool 125 into the work space. In some examples, one or more of these tasks is performed by an assistant, a primary operator, and/or other personnel, with autonomous and/or semi-autonomous support from motion control module 160. For simplicity, the following discussion is in the context of an assistant near the workspace; it should be understood that the discussion is also applicable when other personnel near the workspace (e.g. the primary operator, another person, and/or the like is facilitating the tool exchange.)

In some embodiments, however, the exchange of second tool 125 to replace the first tool 125 may be compounded by the geometries of computer-assisted device 110 and/or the workspace in which computer-assisted device 110 is operating. In some examples, repositionable arm 120 on which second tool 125 is being exchanged to replace first tool 125 may be difficult to reach as it may be positioned among other repositionable arms 120 and/or other tools 125 making access difficult and/or with little clearance around repositionable arm 120 to perform the tool exchange. In some examples, computer-assisted device 110 and/or repositionable arm 120 may be located on an opposite side of the workspace (e.g., on an opposite side of a patient and/or medical table in medical examples) from the assistant. In some examples, this may require the assistant to reach across the workspace, which may increase the risk of contamination of the workspace, a likelihood of the assistant colliding with one of the repositionable arms 120 and/or tools 125, and/or the like. In some examples, the distance across the workspace may be too large and the assistant may have to walk around the workspace to perform the tool exchange. In some examples, the assistant may also have other duties including holding/stabilizing other tools (e.g., a laparoscopic tool inserted into the patient in a medical example), making it difficult for the assistant to reach repositionable arm 120 to perform the tool exchange.

Accordingly, it would be advantageous for computer-assisted system 100 and motion control module 160 to reorient and/or reposition repositionable arm 120 on which the tool exchange is desired so that repositionable arm 120 is positioned and/or oriented within reach of the assistant and/or other personnel so as to better facilitate the tool exchange. It would be equally advantageous for computer-assisted system 100 and motion control module 160 to perform this reorienting and/or repositioning of repositionable arm 120, while keeping repositionable arm docked to the workspace (e.g., to a cannula inserted into the patient in a medical example) and/or while avoiding collisions with other repositionable arms 120, tools 125, and/or obstacles in the vicinity of the workspace.

Figure 2:
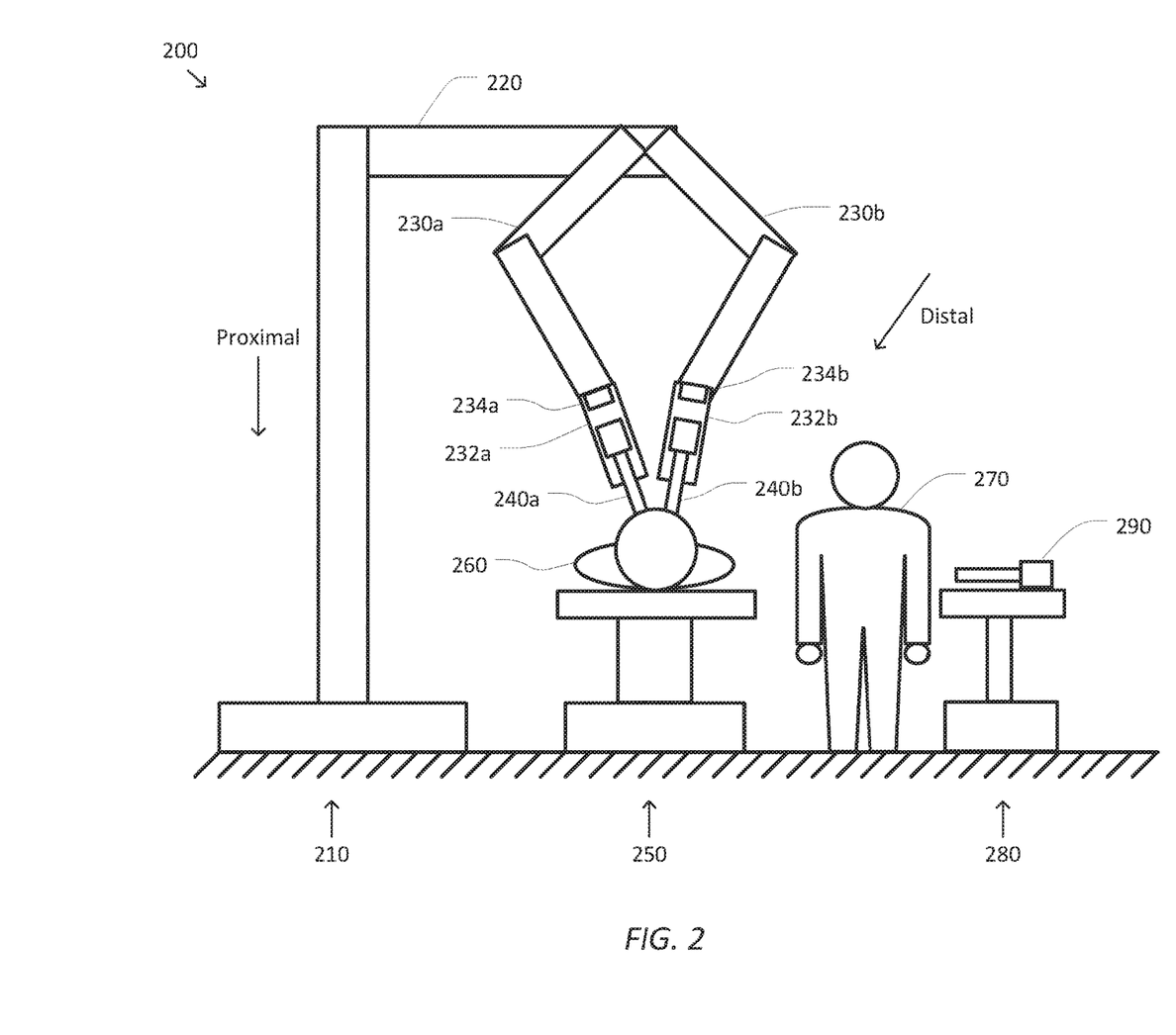
FIG. 2 is simplified diagram of a computer-assisted medical system according to some embodiments.

FIG. 2 is simplified diagram of a computer-assisted medical system 200 according to some embodiments. In some embodiments, computer-assisted medical system 200 may be consistent with computer-assisted system 100. In some embodiments, computer-assisted medical system 200 is a computer-assisted surgical system configured for surgical operations.

As shown in FIG. 2, computer-assisted medical system 200 includes a patient-side computer-assisted medical device 210. As shown, computer-assisted medical device 210 includes a base located on a floor of a room (e.g., an operating room, an interventional suite, and/or the like). Computer-assisted medical device 210 further includes a support structure 220 to which two repositionable arms 230a and 230b are mounted. In some examples, support structure 220 may be used to position and/or orient repositionable arms 230a and 230b relative to a workspace. Each of repositionable arms 230a and 230b includes a respective manipulator 232a or 232b. And although each of repositionable arms 230a and 230b are shown with respective manipulator 232a or 232b, it is understood the repositionable arm and manipulator combination may be a single integrated unit characterized as a repositionable arm or as a manipulator. In some examples, manipulators 232a and 232b may be mounted near a distal end of respective repositionable arm 230a or 230b. In some examples, each of manipulators 232a and 232b may be repositionable having one or more degrees of freedom that allow respective manipulator 232a or 232b to be positioned and/or oriented relative to repositionable arm 230a and 230b, respectively. In some examples, each of manipulators 232a and 232b may include a respective sensing unit 234a or 234b that may be used by computer-assisted medical device 210 to detect and/or track other objects within the workspace as is discussed in further detail below.

To facilitate flexible operation of computer-assisted medical device 210, each of manipulators 232a and 232b is configured with a mechanical and/or electrical interface that allows different kinds of tools (e.g., tools 240a and 240b) to be mounted thereon. Examples of manipulators that support the mounting of different tools are described in further detail in U.S. Pat. App. Pub. No. 2016/0361126, U.S. Pat. App. Pub. No. 2015/0257841, and U.S. Pat. App. Pub. No. 2014/0276951, each of which are incorporated by reference. Tools 240a and 240b may include instruments, imaging devices, and/or the like. In some examples, the instruments may include clamps, grippers, retractors, cautery tools, suction tools, suturing devices, and/or the like. In some examples, the imaging devices may include endoscopes, cameras, ultrasonic devices, fluoroscopic devices, and/or the like.

As further shown in FIG. 2, tools 240a and 240b are being used to perform a procedure on a patient 260 located on a medical table 250. In some examples, a respective shaft of each of tools 240a and/or 240b may be inserted into an interior anatomy of patient 260 through an incision and/or a natural orifice so that end effectors of tools 240a and/or 240b may be used to perform a procedure on the interior anatomy. Although not shown, in some examples, each of manipulators 232a and 232b may be docked to a cannula inserted through the incision and/or the natural orifice. In some examples, the location where the cannula passes through the incision and/or the natural orifice may correspond to a remote center of motion for the respective manipulator 232a and/or 232b and/or the respective tool 240a and/or 240b, which is generally held stationary during a procedure to avoid placing too much stress on the incision and/or the natural orifice. In some examples, the position of the remote center of motion is held fixed, but the orientation of the shaft of the respective tool 240a and/or 240b may be rotated about the remote center of motion and/or inserted and/or retracted relative to the remote center of motion.

Computer-assisted medical system 200 further includes a tool holding device in the form of a tool tray 280 on which one or more additional tools 290 are located. And although tool tray 280 is shown with a tray surface on which the one or more additional tools 290 rest, tool tray 280 may alternatively be a tool rack with one or more holders configured to hold a respective one of the one or more additional tools 290. Other examples of tool holding devices include tool racks, tool hangers, tool holders, tool holsters, drawers, table tops, and/or the like. In some examples, the tool holding devices may be stationary, manually adjustable, adjustable via teleoperation and/or actuation, and/or the like.

In some embodiments, during operation of computer-assisted medical device 210, assistant 270 may exchange one of the one or more additional tools 290 for either of tools 240a or 240b, exchange tools 240a and 240b between manipulators 232a and 232b, and/or the like as is described in further detail below.

According to some embodiments, each of sensing units 234a and/or 234b may include one or more sensing modalities including modalities based on visual, aural, radio-frequency, near-field communication, and/or the like. In some examples, the one or more sensing modalities may be used to identify one or more relevant objects, one or more features of the relevant objects, one or more active emitters on the relevant objects, one or more fiducial markers on the relevant objects, and/or the like. In some examples, the one or more relevant objects may include assistant 270, a portion of the anatomy of assistant 270 (e.g., a hand), tool tray 280, a source of a replacement tool, a remote control device, and/or the like. In some examples, the one or more sensing modalities may be used to detect a direction of a relevant object, a distance to a relevant object, a position of a relevant object, an orientation of a relevant object, and/or the like using a method, such as triangulation.

In some examples, when sensing units 234a and/or 234b include one or more imaging devices, the one or more imaging devices may be used to capture one or more images of areas around manipulator 232a and/or 232b. In some examples, the one or more imaging devices may include a monoscopic camera, a stereoptic camera, a 2D camera, a 3D camera, a ranging unit, and/or the like). In some examples, the one or more imaging devices may include respective wide-angle lenses to provide sensing units 234a and/or 234b with an ability to sense objects at a broad range of orientations relative to manipulators 232a and/or 232b. In some examples, the images captured by the one or more imaging devices may be analyzed to identify the one or more relevant objects. In some examples, the one or more relevant objects may be identified based on detected features of the relevant objects, detected shapes of the relevant objects, indicia on the relevant objects, one or more colors of the relevant objects, one or more reflective elements on the relevant objects, one or more active emitters on the relevant objects, one or more fiducial markers on the relevant objects, and/or the like. In some examples, the relevant objects may include a hand of assistant 270, a gesture of assistant 270, tool tray 280, a source of a replacement tool, the replacement tool, and/or the like. In some examples, each of sensing units 234a and/or 234b may include one or more active emitters that may be used to illuminate areas around manipulators 232a and/or 232b, trigger reflectance in the one or more reflective elements, and/or the like.

In some examples, the ranging unit may determine a distance to an object, which may be used to identify an object and/or to determine the position and/or orientation of the object relative to the ranging unit, by using ultrasonic waves, infrared, and/or the like.

In some examples, when sensing units 234a and/or 234b include one or more audio devices, such as a microphone (e.g. a non-directional or a directional microphone), and/or the like, the audio detected by the one or more audio devices may be analyzed to detect characteristic sounds emitted by assistant 270, one or more active sound emitters, one or more fiducial markers cts, a remote control device, and/or the like. In some examples, the analyzed sounds may be used to identify a command issued by the assistant, such as a voice command, a finger snap, a clap, a click, and/or the like.

In some examples, when sensing units 234a and/or 234b include one or more sensors for detecting signals such as radio-frequency signals, near-field communication signals, and/or the like, the signals captured by the one or more sensors may be analyzed to detect characteristic signals emitted by one or more active emitters, one or more fiducial markers, a remote control device, and/or the like. In some examples, the analyzed signals may be used to identify a command and/or message issued by the one or more active emitters and/or fiducial markers, the remote control device, and/or the like.

As discussed above and further emphasized here, FIG. 2 is merely an example which should not unduly limit the scope of the claims. One of ordinary skill in the art would recognize many variations, alternatives, and modifications. According to some embodiments, other configurations and arrangements of computer-assisted medical system 200 are possible. In some examples, computer-assisted medical device 210 may alternatively be wall-mounted, ceiling mounted, mounted to medical table 250, and/or the like. In some examples, computer-assisted medical device 210 may have a different number of repositionable arms 234, such as one, three, four, and/or five or more.

In some embodiments, sensing units 234a and/or 234b may be located at other locations relative to computer-assisted medical system 200. In some examples, sensing units 234a and/or 234b may be located on repositionable arm 230a or 230b, on support structure 220, on computer-assisted medical device 210, and/or elsewhere within the room (e.g., on the wall and/or ceiling) where computer-assisted medical system 200 is being operated. In some examples, sensing units 234a and 234b may be integrated into a single sensing unit, tracking system, and/or the like. In some examples, the single sensing unit and/or tracking system may include multiple sensors located throughout the room where computer-assisted medical system 200 is being operated. In some examples, each of sensing units 234a and/or 234b may include two or more sensing devices located together and/or separately.

In some embodiments, one or both of sensing units 234a or 234b may be located on either assistant 270 and/or tool tray 280. In some examples, when a sensing unit is located on assistant 270 and/or tool tray 280, the sensing unit may be used to locate and/or track manipulator 232a and/or 232b, tools 240a and/or 240b, and/or the like by detecting their respective shapes, fiducial markers, active emitters, reflective elements, and/or the like using techniques similar to those discussed previously with respect to assistant and/or tool tray detection and/or tracking. In some examples, when the sensing unit is located on assistant 270, the sensing unit may be a wearable sensing unit (e.g., a badge and/or the like), part of an augmented and/or virtual reality system (e.g., as part of a handheld, console-located, head-mounted, and/or other display), and/or the like. In some examples, status of a tool exchange may be displayed on the head-mounted display to aid the assistant in working with the computer-assisted medical device 210 to perform the tool exchange. In some embodiments, sensing units 234a and/or 234b may be supplemented by a sensing unit located on assistant 270, tool tray 280, tool 125, and/or the like.

Figure 3:
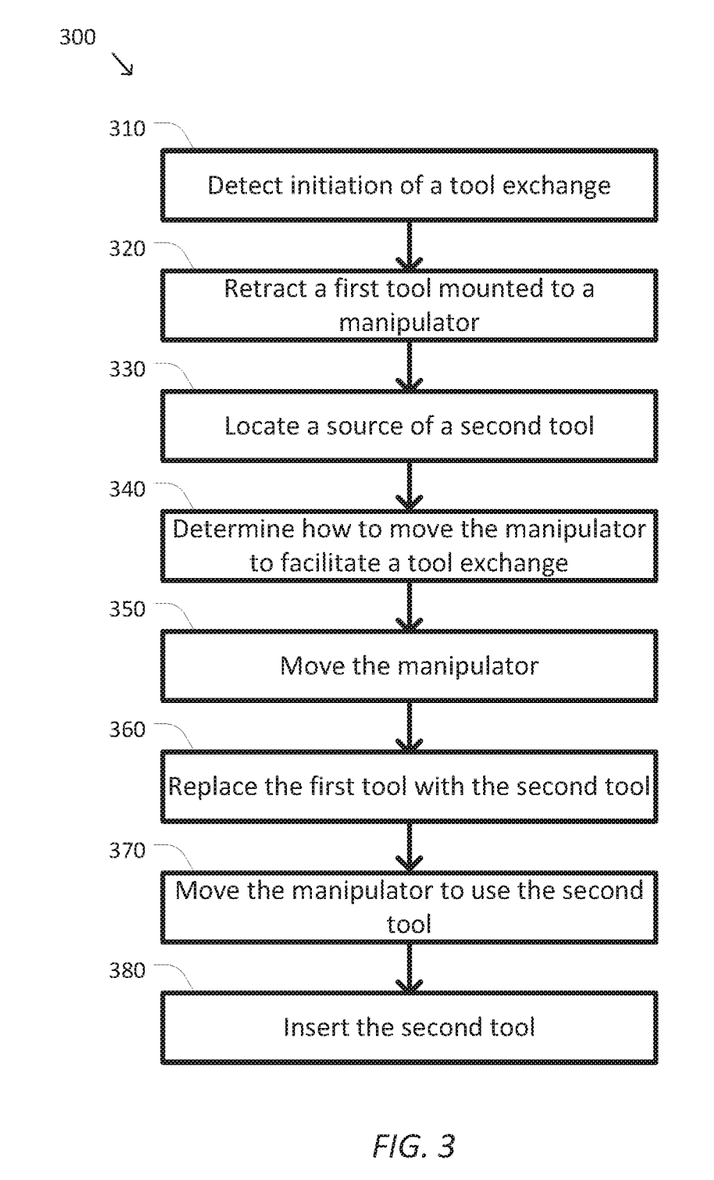
FIG. 3 is a simplified diagram of a method of assisting tool exchange according to some embodiments.

FIG. 3 is a simplified diagram of a method of assisting tool exchange according to some embodiments. One or more of the processes 310-380 of method 300 may be implemented, at least in part, in the form of executable code stored on non-transitory, tangible, machine-readable media that when run by one or more processors (e.g., the processor 140 in control unit 130) may cause the one or more processors to perform one or more of the processes 310-380. In some embodiments, portions of method 300 may be performed by a module, such as motion control module 160. In some embodiments, method 300 may be used to facilitate an exchange of tools (e.g., tools 240a, 240b, and/or 290) on a manipulator (e.g., manipulator 232a and/or 232b) of a computer-assisted device (e.g., computer-assisted device 110 and/or computer-assisted medical device 210) by an assistant (e.g., assistant 270).

In some embodiments, one or more of the processes of method 300 may be performed in a different order than the order implied by the flow chart in FIG. 3. In some examples, processes 330-350 may be performed repeatedly in a loop until movement of the manipulator is complete. In some examples, process 330 may be performed concurrently with process 320. In some examples, process 320 may be performed concurrently with processes 330, 340, and/or 350. In some examples, process 380 may be performed concurrently with process 370. In some examples, one or more of processes 320 and/or 380 are optional and may be omitted. In some examples, process 370 may begin before the second tool is mounted to the manipulator during process 360.

Figure 4:
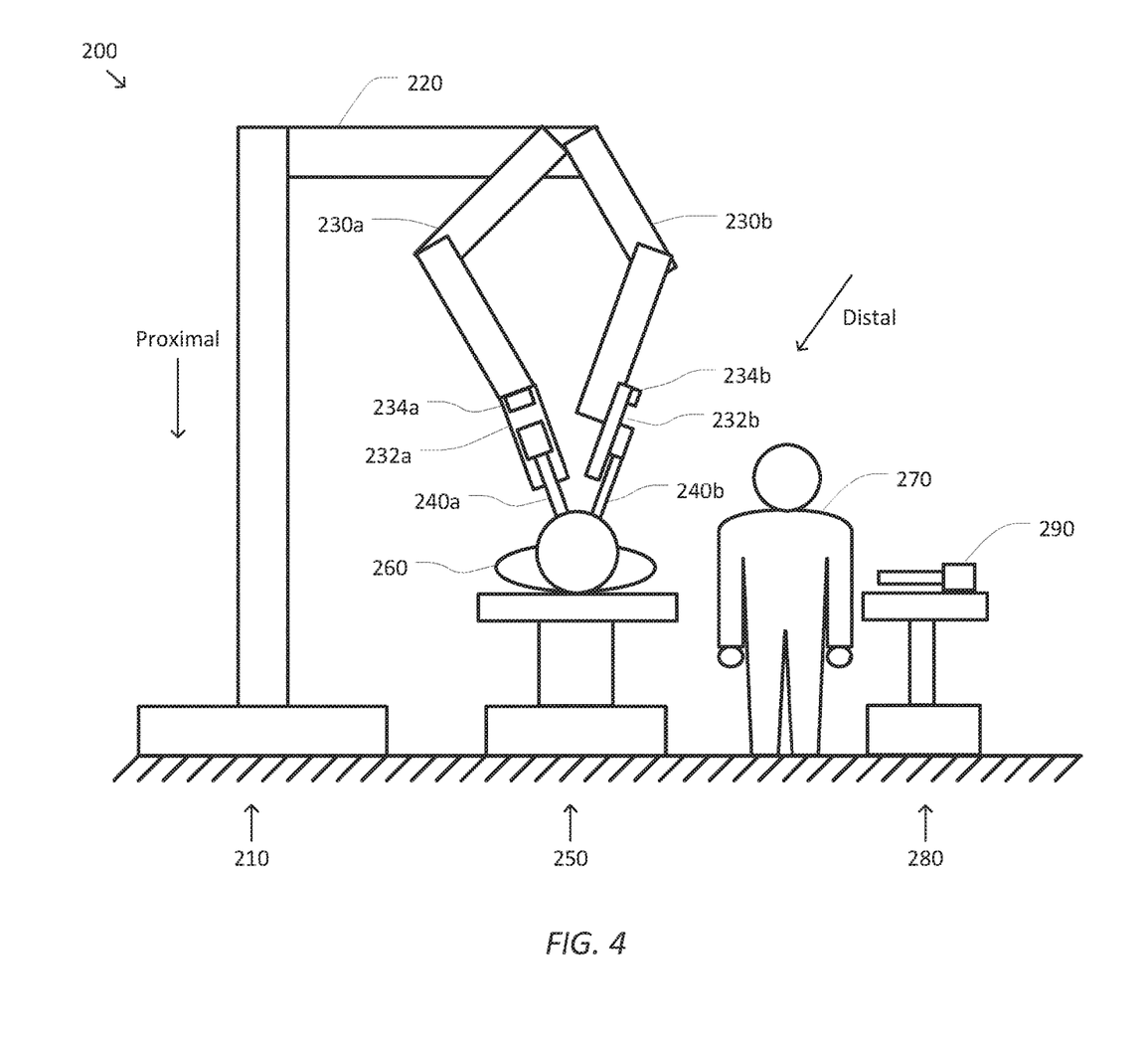
FIGS. 4 and 5 are simplified diagrams of a computer-assisted medical system during a tool exchange according to some embodiments.
Figure 5:
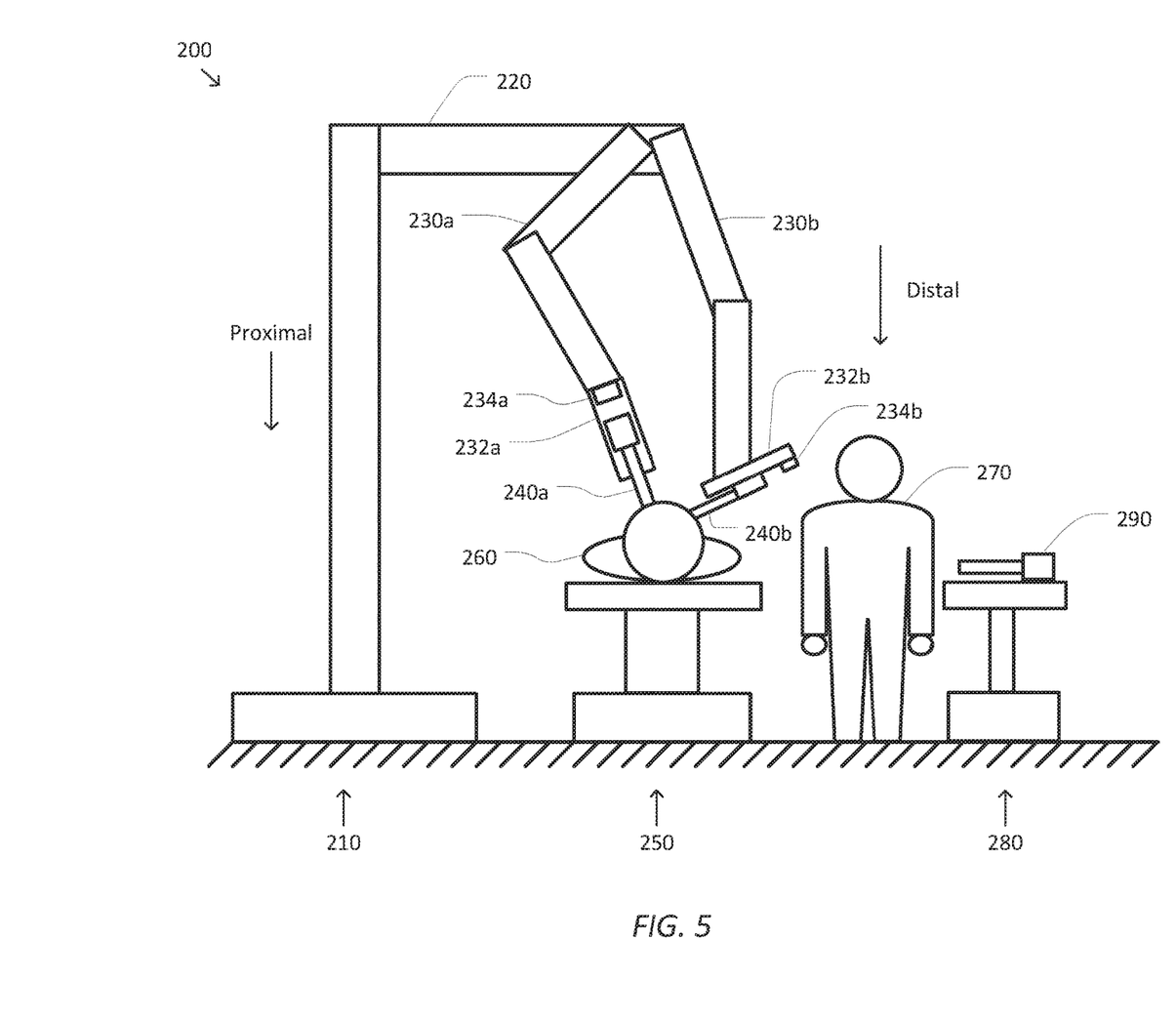

In order to help illustrate the processes of method 300, method 300 is described by reference to FIGS. 2, 4 and 5, which are simplified diagrams of computer-assisted medical system 200 during various stages of a tool exchange according to some embodiments. However, it is understood that references to FIGS. 2, 4, and 5 are exemplary only and that method 300 may be performed using other computer-assisted medical systems and/or non-medical computer-assisted systems.

At a process 310, initiation of a tool exchange is detected. In some examples, initiation of the tool exchange is indicated by an operator, such as assistant 270, an operator at a console used to teleoperate the computer-assisted device, and/or the like. In some examples, the initiation of the tool exchange is indicated by the activation of an input control (e.g., a button, a lever, a pedal, a touch screen, and/or the like on the computer-assisted device, the manipulator, the operator console, a tablet device, a pendant device, a tool tray and/or tool rack (such as tool tray 280), and/or the like). In some examples, the initiation of the tool exchange is indicated by pressing a button on a remote control device. In some examples, the initiation of the tool exchange is indicated by an audio command, such as a click, a finger snap, a clap, a voice command (e.g., "swap tool", "initiate tool exchange," "come to me", and/or the like), and/or the like. In some examples, the initiation of the tool exchange may be indicated by a gesture, such as a gesture performed by assistant 270. In some examples, the gesture may include a hand out and open with a palm up, a hand out with the palm down, a hand in a pose similar to a pose used to mount a tool to a manipulator, a hand wave, a finger snap, a hand clap, and/or the like.

In some embodiments, the initiation of the tool exchange may be detected by one or more sensing units, such as sensing units 234a and/or 234b. In some examples, the one or more sensing units may capture one or more images, one or more sounds, and/or one or more signals that may be analyzed to detect the initiation of the tool exchange using any appropriate technique as described previously with respect to FIG. 2.

In some embodiments, the initiation of the tool exchange may include other information that further describe the desired tool exchange. In some examples, the other information may include one or more of a manipulator on which the tool exchange is to occur, a desired replacement tool (e.g., to use to confirm a correct tool exchange), a source of the replacement tool and/or the like. In some examples, the source of the replacement tool may correspond to assistant 270, tool tray 280, a tool rack, and/or the like.

In the examples of FIGS. 2, 4, and 5, FIG. 2 depicts computer-assisted medical system 200 during process 310 and before performance of the initiated tool exchange occurs.

At an optional process 320, a first tool mounted to the manipulator is retracted. In some examples, when the tool exchange is initiated, the first tool that is currently mounted to the manipulator may be inserted into the workspace so that it can be used to perform one or more tasks. In some examples, first tool may be inserted through a cannula and/or an access port past a remote center of motion of the first tool and it may difficult to dismount the first tool from the manipulator without retracting the first tool. In some examples, leaving the first tool inserted during further portions of method 300 may increase a risk of the first tool damaging material in the workspace (e.g., tissue of a patient in medical embodiments) when the first tool is rotated about the remote center of motion. In some examples, these difficulties and/or risks may be reduced by retracting the first tool so that its distal-most portion is proximal to the remote center of motion, the cannula, the access port, the material in the workspace (e.g., the tissue of the patient in medical embodiments), and/or the like. In some examples, the first tool may be retracted by an operator (e.g., via teleoperation), manually by the assistant, and/or autonomously by the computer-assisted device. In some examples, the first tool may be retracted by commanding one or more actuators used to control an insertion degree-of-freedom for the first tool. In some examples, the one or more actuators may be commanded using one or more signals, such as one or more voltages, one or more currents, one or more pulse-width modulated waveforms, and/or the like.

At a process 330, a source of a second tool (e.g., the tool replacing the first tool) is located. In some examples, the location of the source of the second tool may be determined using one or more sensing units, such as the one or more sensing units from process 310, sensing unit 234a, sensing unit 234b, and/or any of the other sensing and tracking units described with respect to the embodiments of FIG. 2. In some examples, the location of the source of the second tool may be determined from one or more images, one or more sounds, and/or one or more signals detected and/or captured by the one or more sensing units. In some examples, the one or more images, the one or more sounds, and/or the one or more signals may be analyzed to detect the location of the source of the second tool. In some examples, the location of the source of the second tool may be indicated by a location of one or more shapes, indicia, fiducial markers, active emitters, reflective markers, remote control devices, and/or the like located at, on, or near the source of the second tool. In some examples, the location of the source of the second tool may correspond to a hand of the assistant (e.g., the hand detected during process 310 and/or the hand performing the gesture detected during process 310), the remote control device used to initiate the tool exchange as detected during process 310, a tool tray and/or rack (e.g., tool tray 280), the second tool, and/or the like. In some examples, the one or more images, the one or more sounds, and/or the one or more signals may be analyzed using any appropriate technique as described previously with respect to FIG. 2, such as shape detection, tracking, triangulation, and/or the like. In some examples, the location of the source of the second tool may be determined indirectly using one or more sensing units associated with the assistant, the tool tray, the tool rack, and/or the second tool by detecting a location of the manipulator and/or the first tool relative to the sensing unit as previously described with respect to FIG. 2. In some examples, the location of the source of the second tool may be a location of a most recent or other previous tool exchange, a location of where the first tool was previously mounted to the manipulator, a location of the source of a most recent or other previous tool exchange, a location of the source of the first tool before it was mounted to the manipulator, and/or the like. In some examples, the location of the source of the second may be determined based on analysis of the kinematics of the computer-assisted device, the repositionable arm, the manipulator, and/or the first tool when the first tool was previously mounted to the manipulator.

According to some embodiments, process 330 may identify multiple possible sources for the location of the second tool. In some examples, these multiple possible sources may be associated with multiple assistants and/or other persons detected in the workspace, a person and a tool tray and/or tool rack in the workspace, multiple tools trays tool racks, and/or the second tool in the workspace, multiple remote control devices, multiple fiducial markers, multiple emitters, multiple reflective markers, multiple indicia, and/or the like and/or combinations thereof. In some examples, one or more rules may be used to determine which of the multiple possible sources is the most likely source for the location of the second tool. In some examples, the one or more rules may select a location co-located with the provider (e.g., the assistant, the operator, and/or the like) of the indication of the tool exchange and/or identified in the indication of the tool exchange (e.g., by the operator when initiating the tool exchange). In some examples, the one or more rules may be used to determine which of the multiple possible sources based on identifying the second tool. In some examples, the one or more rules may select a location associated with the assistant, the tool tray, and/or the tool rack used for a most recent or other previous tool exchange. In some examples, the one or more rules may select a location that it within a predefined area within the workspace, that is closest to the manipulator when the tool exchange was initiated, and/or the like. In some examples, the one or more rules may include prompting the operator and/or the assistant to select from among the multiple possible sources.

At a process 340, a motion plan for determining how to move the manipulator to facilitate the tool exchange is determined. In some examples, the motion plan may include determining a configuration of the manipulator and/or the repositionable arm to which the manipulator is mounted that positions and/or orients the manipulator with a position and/or orientation that is closer to and/or more appropriately oriented to the location of the second tool and/or the assistant who will perform the tool exchange. In some examples, the determined configuration may be determined based on a type of the location of the second tool such that the determined configuration when the location of the tool is the hand of the assistant may be different than the determined configuration for the tool tray and/or tool rack.

In some embodiments, the motion plan may include determining one or more motions of the manipulator and/or the repositionable arm that move the manipulator from its position and/or orientation after processes 310 and/or 320 to the determined configuration. In some examples, the one or more motions may be determined based on one or more kinematic models of the manipulator and/or the repositionable arm and the determined configuration. In some examples, the one or more motions may include a single motion from the position and/or orientation of the manipulator after processes 310 and/or 320 and the determined configuration. In some examples, the one or more motions may include a sequence of motions.

In some embodiments, when the manipulator and/or the first tool are constrained to preserve the remote center of motion (e.g., when the manipulator is docked to a cannula or access port), the one or more motions may include rotating the manipulator and the first tool about a vertical axis through the remote center of motion so that the manipulator and the proximal end of the first tool are rotated toward the location of the source of the second tool. In the examples of FIGS. 2, 4, and 5, FIG. 4 depicts computer-assisted medical system 200 after performing the rotation about the vertical axis so that tool 240b is between manipulator 232b and assistant 270. The one or more motions may further include rotating the manipulator and the first tool so that they point toward the source of the second tool, such as by rotating the manipulator and the first tool about a horizontal axis through the remote center of motion and perpendicular to an axial axis of the shaft of the first tool. In the examples of FIGS. 2, 4, and 5, FIG. 5 depicts computer-assisted medical system 200 after performing the rotation about the horizontal axis so that the proximal end of tool 240b is pointed toward assistant 270. In some examples, the order of the vertical and horizontal rotations may be reversed, may occur concurrently, may include alternations between vertical and horizontal rotations, and/or the like.

In some embodiments, when the manipulator and/or the first tool are not constrained to preserve the remote center of motion, the one or more motions may include one or more translations of the manipulator and/or the first tool to move them toward the determined configuration.

According to some embodiments, the motion plan determined during process 340 may take advantage of redundant degrees of freedom in the repositionable arm, the manipulator, and/or the first tool, and/or a null space of a Jacobian in the kinematics of the repositionable arm, the manipulator, and/or the first tool. In some examples, the redundant degrees of freedom and/or the null space allow the motion plan to include one of a plurality of joint positions and/or motions that may each move the manipulator and/or the first tool into a desired position and/or orientation. In some examples, the choice of the joint positions and/or motions may be selected to minimize a cost function, such as a total distance moved by the manipulator and/or the first tool to reach the desired configuration, to avoid range of motion limits in the joints of the manipulator and/or the first tool, and/or the like.

According to some embodiments, the motion plan determined during process 340 may include a collision-free path around obstacles in the workspace. In some examples, the obstacles may include one or more other repositionable arms, other manipulators, other tools, material in the workspace (e.g., the patient), the assistant, other assistants, the tool tray, and/or the like. In some examples, the collision-free path may include one or more motions that may move the repositionable arm, the manipulator, and/or the first tool so that they avoid the obstacles. In some examples, one or more of the one or more motions that avoid the collisions may not move the manipulator and the first tool toward the determined configuration.

According to some embodiments, the motion plan determined during process 340 may include motions of one or more of the other repositionable arms, the other manipulators, and/or the other tools to generate the collision-free path. In some examples, the one or more motions may take advantage of the redundant degrees of freedom and/or the null spaces of the other repositionable arms, the other manipulators, and/or the other tools so as not to disturb positions and/or orientations of the distal ends of the other tools during the motions. In some examples, the one or more motions may include motions of the repositionable arm, the manipulator, and/or the first tool interspersed and/or contemporaneous with the motions of the other repositionable arms, the other manipulators, and/or the other tools. As an example, the repositionable arm, the manipulator, and/or the first tool may first be moved out of the way, the other repositionable arms, the other manipulators, and/or the other tools may then be moved, and then the repositionable arm, the manipulator, and/or the first tool may be moved to the determined configuration.

At a process 350, the manipulator and the first tool are moved according to the motion plan determined during process 340 so that the manipulator and the first tool are moved into the configuration determined during process 340. In some examples, the motion plan may be performed by commanding one or more actuators in the repositionable arm, the manipulator, the first tool, the other repositionable arms, the other manipulators, and/or the other tools to perform the one or more motions in the motion plan. In some examples, the one or more actuators may be commanded using one or more signals, such as one or more voltages, one or more currents, one or more pulse-width modulated waveforms, and/or the like.

In the examples of FIGS. 2, 4, and 5, FIG. 4 and FIG. 5 depicts computer-assisted medical system 200 during the movements of process 350 as previously discussed with respect to process 340.

In some examples, the motion plan may be started automatically after it is planned and/or may be delayed until a movement initiating event is detected. In some examples, the movement initiating event may include one or more of activation of an input by the operator and/or the assistant, detection of a gesture, detection of sound command, and/or the like. In some examples, the movement initiating event may be detected using any of the techniques described with respect to process 310 used to detect the initiation of the tool exchange.

In some embodiments, the movements of process 350 may be paused, aborted, and/or adjusted based on monitoring while process 350 is being performed. In some examples, the movements may be paused, aborted, and/or adjusted in response to detecting position and/or velocity errors above a threshold in any of the joints being moved, position and/or velocity errors above a threshold in one or more control points on any of the repositionable arms, the manipulators, and/or the tools being moved. In some examples, the one or more control points may include a remote center a motion, the proximal portion of the first tool being oriented toward the location of the source of the second tool, and/or the like. In some examples, the movements may be paused, aborted, and/or adjusted in response to detecting a force and/or torque meeting a force and/or torque criterion, such as reaching and/or exceeding an upper force and/or torque limit in any of the joints being moved.

At a process 360, the first tool is replaced with the second tool (e.g., the tool exchange occurs). In some examples, process 360 is performed by the assistant. In some examples, process 360 includes dismounting the first tool from the manipulator and then mounting the second tool to the manipulator. In some examples, process 360 further includes detecting engagement of the second tool with the manipulator. In some examples, the engagement of the second tool with the manipulator includes one or more of detecting physical mounting of the second tool to with manipulator, detecting proper electrical connection and/or proper communication between the second tool and the manipulator, successful completion of one or more startup and/or engagement tests, and/or the like. In some examples, completion of the tool exchange may be detected by detecting the mounting of the second tool to the manipulator and/or detecting the engagement of the second tool with the manipulator. In some examples, completion of the tool exchange may be indicated by the assistant and/or the operator and/or based on detecting a tool exchange completion event. In some examples, the tool exchange completion event may include one or more of activation of an input by the operator and/or the assistant, detection of a gesture, detection of sound command, detection of a haptic command, expiration of a timer, and/or the like. In some examples, the tool exchange completion event may be detected using any of the techniques described with respect to process 310 used to detect the initiation of the tool exchange. In some examples, the haptic event may include the assistant performing a double tap and/or the like on the second tool and/or the manipulator.

At a process 370, the manipulator is moved so that the second tool can be used. In some examples, process 370 includes performing the motion plan of process 340 in reverse order into to place the second tool into a working configuration. In some examples, process 370 may begin automatically after detecting the mounting of the second tool to the manipulator and/or may be delayed until the tool exchange completion event is detected during process 370. In some examples, process 370 may begin before the second tool is mounted to the manipulator and/or the second tool is engaged with the manipulator during process 360 such that the mounting of the second tool to the manipulator and/or the engagement between the second tool and the manipulator may occur while the manipulator is being moved so that the second tool can be used.

As an optional process 380, the second tool is inserted. In some examples, the second tool may be inserted by commanding one or more actuators used to control an insertion degree-of-freedom for the second tool. In some examples, the one or more actuators may be commanded using one or more signals, such as one or more voltages, one or more currents, one or more pulse-width modulated waveforms, and/or the like. In some examples, the second tool may be inserted by an operator (e.g., via teleoperation), manually by the assistant, semi-autonomously by the computer assisted device (e.g., by providing virtual and/or haptic assistance to the operator and/or the assistant), and/or autonomously by the computer-assisted device. In some examples, the autonomous insertion by the computer-assisted device may begin automatically after completing process 370 and/or may be delayed until an insertion OK event is detected. In some examples, the insertion OK event may be indicated by the assistant and/or the operator and/or may include one or more of activation of an input by the operator and/or the assistant, detection of a gesture, detection of sound command, and/or the like. In some examples, the insertion OK event may be detected using any of the techniques described with respect to process 310 used to detect the initiation of the tool exchange.

Once method 300 completes, method 300 may be repeated to perform other tool exchanges on the same manipulator and/or on one of the other manipulators.

As discussed above and further emphasized here, FIG. 3 is merely an example which should not unduly limit the scope of the claims. One of ordinary skill in the art would recognize many variations, alternatives, and modifications. According to some embodiments, the processes of method 300 may be applied to support different tool exchange scenarios. In some examples, method 300 may be performed concurrently for two different manipulators so that the tools on the two manipulators may be exchanged at the same time. In some examples, the two different manipulators may be moved toward different sources for the respective second tools (e.g., for exchanging by different assistants). In some examples, the respective motions plans of respective process 340 may include motions that avoid collisions during the concurrent tool exchange.

In some embodiments, method 300 may be adapted to support the exchange of the first tool from a first manipulator to a second manipulator. In some examples, to support the tool exchange between the first and second manipulators, process 330 may be modified to detect the assistant that will be performing the tool exchange during process 360; processes 340, 350, and 360 may be modified to perform motion planning and movement for both the first and second manipulators; process 360 may be modified to include dismounting the first tool from the first manipulator and mounting the second tool to the second manipulator; and/or process 380 may be modified to insert the first tool as mounted to the second manipulator.

In some embodiments, process 360 may include further motions of the manipulator as directed by the assistant and/or the operator. In some examples, the assistant may place the manipulator and/or the repositionable arm in a clutched mode that allows manual movement of the manipulator and/or the repositionable arm toward a more advantageous position and/or orientation for the tool exchange. In some examples, the clutched mode may be activated by pressing a button and/or other input on the manipulator and/or the repositionable arm; exerting manual force against the first tool, the manipulator, and/or the repositionable arm above a force threshold; and/or the like. In some examples, the clutched mode may only allow manual movement that is constrained to preserve the remote center of motion. In some examples, the further motions may be commanded by the operator (e.g., teleoperatively).

In some embodiments, process 360 may be automated. In some examples, when a tool tray and/or tool rack, moveable relative to the medical system, is the source for the second tool and the tool tray and/or the tool rack includes tool holders, process 360 may be automated. In some examples, the automation of process 360 may include dismounting the first tool into a first empty tool holder and then mounting the second tool from a second holder holding the second tool.

Some examples of control units, such as control unit 130 may include non-transitory, tangible, machine readable media that include executable code that when run by one or more processors (e.g., processor 140) may cause the one or more processors to perform the processes of method 300. Some common forms of machine readable media that may include the processes of method 300 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
   a manipulator comprising one or more actuators and configured to have at least one tool of multiple tools mounted thereon; and one or more processors coupled to the manipulator and configured to:
  detect initiation of a tool exchange; and
  in response to detecting the initiation of the tool exchange, perform a set of steps to:
    determine a location of a source of a replacement tool to be mounted to the manipulator;
    determine, based on the location of the source, a computed configuration of the manipulator for when the tool exchange is performed, wherein the computed configuration is different from a current configuration of the manipulator when the tool exchange is initiated and facilitates mounting of the replacement tool to the manipulator, wherein the computed configuration of the manipulator includes at least one of a position of the manipulator or an orientation of the manipulator;
    determine a motion plan that moves the manipulator from the current configuration into the computed configuration; and
    command movement of the manipulator into the computed configuration according to the motion plan via signals applied to the one or more actuators of the manipulator.

2. The computer-assisted device of claim 1, wherein:
the computer-assisted device is a medical device; and
the replacement tool is a medical tool.

3. The computer-assisted device of claim 1, wherein the one or more processors are configured to determine the computed configuration further based on a type of the source of the replacement tool.

4. The computer-assisted device of claim 1, wherein to determine the location of the source of the replacement tool, the one or more processors are configured to locate at least a part of an assistant or of a tool holding device.

5. The computer-assisted device of claim 1, wherein:
a first tool is mounted to the manipulator when the initiation of the tool exchange is detected; and
the one or more processors are further configured to command retraction of the first tool along an insertion degree of freedom of the first tool before commanding the movement of the manipulator into the computed configuration.

6. The computer-assisted device of claim 1, wherein to determine the location of the source of the replacement tool, the one or more processors are configured to determine:
a direction of the source of the replacement tool relative to the manipulator; or
a position of the source of the replacement tool; or
an orientation of the source of the replacement tool.

7. The computer-assisted device of claim 1, wherein to determine the location of the source of the replacement tool, the one or more processors are configured to determine the source of the replacement tool from the initiation of the tool exchange.

8. The computer-assisted device of claim 7, wherein to determine the source of the replacement tool from the initiation of the tool exchange, the one or more processors are configured to:
determine a location of the initiation of the tool exchange; or
determine a provider of the initiation of the tool exchange; or
select the source of the replacement tool from a plurality of possible sources of the replacement tool.

9. The computer-assisted device of claim 8, wherein to select the source of the replacement tool from the plurality of possible sources of the replacement tool, the one or more processors are configured to identify the replacement tool.

10. The computer-assisted device of claim 1, wherein:
to determine the location of the source of the replacement tool, the one or more processors are configured to locate a source of a previous tool for the computer-assisted device.

11. The computer-assisted device of claim 10, wherein the previous tool was mounted to the manipulator before the initiation of the tool exchange is detected.

12. The computer-assisted device of claim 1,
wherein the motion plan comprises:
a motion to rotate the manipulator about a vertical axis through a remote center of motion of the manipulator; and
a motion to rotate the manipulator about a horizontal axis through the remote center of motion.

13. The computer-assisted device of claim 1,
wherein the motion plan comprises a motion of a second manipulator; and
the one or more processors are further configured to command the motion of the second manipulator according to the motion plan.

14. The computer-assisted device of claim 1, wherein the one or more processors are further configured to command movement of the replacement tool into a working configuration after the tool exchange.

15. The computer-assisted device of claim 14, wherein the one or more processors are further configured to automatically command insertion of the replacement tool along an insertion degree of freedom after the replacement tool has moved into the working configuration.

16. The computer-assisted device of claim 1, wherein the one or more processors are further configured to:
dismount an old tool mounted to the manipulator to a first tool holder; and
mount the replacement tool to the manipulator from a second tool holder.

17. The computer-assisted device of claim 1, wherein the one or more processors are further configured to stop the commanded movement of the manipulator to the computed configuration in response to:
a command received from an operator;
a position or velocity error associated with a control point or a joint of the manipulator or the computer-assisted device that is above a threshold; or
a force or torque of the manipulator or the computer-assisted device meeting a force or torque criterion.

18. A method comprising:
detecting, by one or more processors, initiation of a tool exchange; and
in response to detecting the initiation of the tool exchange, perform a set of steps including:
determining, by the one or more processors, a location of a source of a replacement tool to be mounted to a manipulator of a computer-assisted device, wherein the manipulator comprises one or more actuators;
determining, by the one or more processors based on the location of the source, a computed configuration of the manipulator for when the tool exchange is performed, wherein the computed configuration is different from a current configuration of the manipulator when the tool exchange is initiated, wherein the computed configuration facilitates mounting of the replacement tool to the manipulator, wherein the computed configuration of the manipulator includes a least one of a position of the manipulator or an orientation of the manipulator;

determining a motion plan that moves the manipulator from the current configuration into the computed configuration; and commanding, by the one or more processors, movement of the manipulator into the computed configuration according to the motion plan via signals applied to the one or more actuators of the manipulator.

19. The method of claim 18, wherein the determining of the computed configuration is further based on a type of the source of the replacement tool.

20. The method of claim 18, wherein determining the location of the source of the replacement tool comprises locating at least a part of an assistant or of a tool holding device.

21. The method of claim 18, wherein:

a first tool is mounted to the manipulator when the initiation of the tool exchange is detected; and the method further comprises commanding retraction of the first tool along an insertion degree of freedom of the first tool before commanding the movement of the manipulator into the computed configuration.

22. The method of claim 18, wherein determining the location of the source of the replacement tool comprises determining the source of the replacement tool from the initiation of the tool exchange.

23. The method of claim 18, wherein determining the location of the source of the replacement tool comprises locating a source from which a first tool was received, the first tool having been mounted to the manipulator before the initiation of the tool exchange is detected.

24. The method of claim 18, wherein the motion plan comprises:

a motion of a second manipulator;

a motion to rotate the manipulator about a vertical axis through a remote center of motion of the manipulator; and a motion to rotate the manipulator about a horizontal axis through the remote center of motion; and the method further comprises commanding the motion of the second manipulator according to the motion plan.

25. The method of claim 18, further comprising commanding movement of the replacement tool into a working configuration after the tool exchange.

26. A non-transitory machine-readable medium comprising a plurality of machine-readable instructions which when executed by one or more processors associated with a computer-assisted device are adapted to cause the one or more processors to perform a method comprising:

detecting initiation of a tool exchange; and in response to detecting the initiation of the tool exchange, perform a set of steps including:

determining a location of a source of a replacement tool to be mounted to a manipulator of a computer-assisted device, wherein the manipulator comprises one or more actuators;

determining, based on the location of the source, a computed configuration of the manipulator for when the tool exchange is performed, wherein the computed configuration is different from a current configuration of the manipulator when the tool exchange is initiated, wherein the computed configuration facilitates mounting of the replacement tool to the manipulator, wherein the computed configuration of the manipulator includes a least one of a position of the manipulator or an orientation of the manipulator;

determining a motion plan that moves the manipulator from the current configuration into the computed configuration; and commanding movement of the manipulator into the computed configuration according to the motion plan via signals applied to the one or more actuators of the manipulator.

27. The non-transitory machine-readable medium of claim 26, wherein determining the location of the source of the replacement tool comprises:

locating at least a part of an assistant; or locating a tool holding device; or determining the source of the replacement tool from the initiation of the tool exchange.

* * * * *